(12) United States Patent
Tilzer et al.

(10) Patent No.: US 10,275,574 B2
(45) Date of Patent: Apr. 30, 2019

(54) RETAIL PHARMACY CUSTOMER RECOGNITION AND SALES

(71) Applicant: CVS Pharmacy, Inc., Woonsocket, RI (US)

(72) Inventors: Brian Tilzer, Cumberland, RI (US); Dustin Wayne Humphreys, East Greenwich, RI (US); Rohit Gupta, Brampton (CA)

(73) Assignee: CVS Pharmacy, Inc., Woonsocket, RI (US)

( * ) Notice: Subject to any disclaimer, the term of this patent is extended or adjusted under 35 U.S.C. 154(b) by 271 days.

(21) Appl. No.: 14/291,779

(22) Filed: May 30, 2014

(65) Prior Publication Data

US 2015/0347715 A1   Dec. 3, 2015

(51) Int. Cl.
*G06F 19/00* (2018.01)
*G06Q 30/02* (2012.01)
*H04W 12/06* (2009.01)
*G06F 16/951* (2019.01)
*H04W 12/02* (2009.01)

(52) U.S. Cl.
CPC ........ *G06F 19/3475* (2013.01); *G06F 16/951* (2019.01); *G06F 19/3456* (2013.01); *G06Q 30/0231* (2013.01); *H04W 12/06* (2013.01); *H04W 12/02* (2013.01)

(58) Field of Classification Search
CPC .... G06F 19/3475; G06Q 50/22; G06Q 50/24; G16H 40/063; G16H 50/20
USPC .......................................................... 705/2
See application file for complete search history.

(56) References Cited

U.S. PATENT DOCUMENTS

| | | | |
|---|---|---|---|
| 2009/0030720 A1* | 1/2009 | Nadas | G06F 19/328 705/2 |
| 2012/0173322 A1* | 7/2012 | Ringewald et al. | G06Q 20/027 |
| 2014/0379371 A1* | 12/2014 | Tran | G06Q 50/22 705/2 |
| 2014/0379467 A1 | 12/2014 | Huang et al. | |

OTHER PUBLICATIONS

WO2015106009;Webb et al., System and Method for dispensing and purchasing medical prescription, Jul. 2015.*

* cited by examiner

*Primary Examiner* — Hiep V Nguyen
(74) *Attorney, Agent, or Firm* — Patent Law Works LLP

(57) ABSTRACT

A retail pharmacy sales system for identifying a customer and identifying which prescriptions the customer is authorized to pick up is disclosed. The system may include a retail pharmacy sales device in communication with a mobile device. The retail pharmacy sales device is configured to identify the customer, receive acknowledgement for the prescriptions, and process the payments for the prescriptions based on communication with the mobile device.

27 Claims, 4 Drawing Sheets

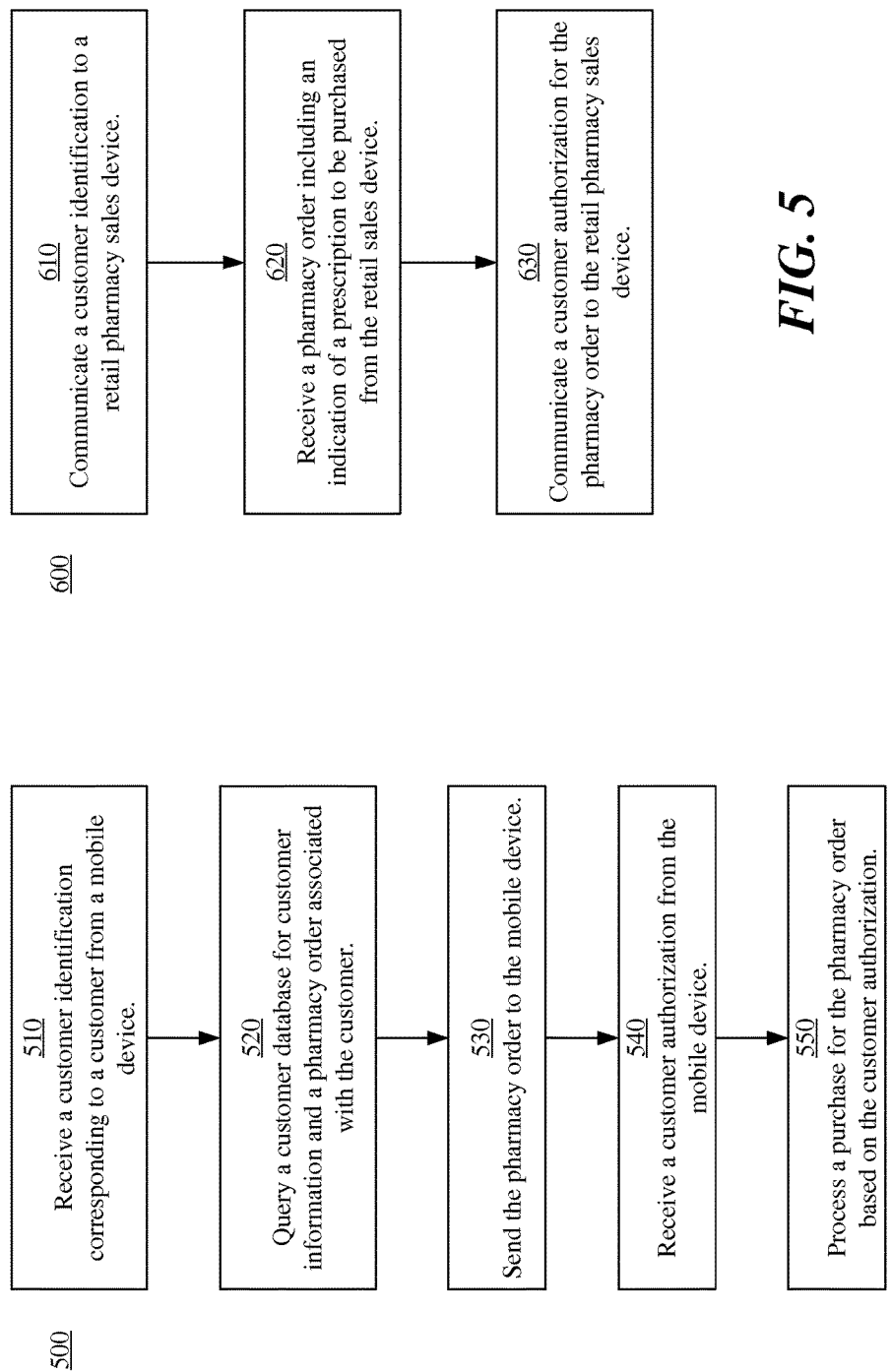

RETAIL PHARMACY CUSTOMER RECOGNITION AND SALES

FIELD OF THE DISCLOSURE

The disclosure relates generally to the field of retail, and more particularly to a system and method for recognizing and selling merchandize to a retail pharmacy customer.

BACKGROUND OF THE DISCLOSURE

The retailing of prescription pharmaceuticals is often highly regulated. For example, in the United States, retailers are regulated by a variety of different government agencies, with the regulations typically varying by state. One common regulation requires that the pharmacy retailer identify the pharmacy customer and ensure that the pharmacy customer is authorized to pick up the prescriptions requested. Today this is a manual process that requires the retailer converse with the customer and request various identifying information from the customer. For example, the retailer may request the customer to provide names and birth dates for the persons to whom the prescriptions are intended. As will be appreciated, this process can be time consuming. Furthermore, due to the manual method of verifying identify of a customer and authorization to pick up prescriptions, customers typically do not use mobile payment solutions to complete the transaction. This adds additional manual steps to the overall transaction, which slows the total time necessary to complete the transaction.

Additionally, it is common for pharmacy retailers to utilize a rewards program whereby customer's purchases can be monitored and the customer may receive various benefits, or rewards, for patronizing a particular retailer. For example, some pharmacy retailers utilize a rewards program whereby customers may receive some benefit (e.g., in-store gift card, coupons, or the like) once the customer has a specified number of prescriptions filled at that retailer. Adding the purchase to a rewards account is also a manual process. For example, customers may carry a rewards card that can be scanned at the point of sale to identify the customer. As another example, customers can manually enter a phone number connected to their rewards account. As another example, customers may use a key chain tag to identify their rewards account. In a specific example, when a customer uses a drive through to pick up a prescription, the customer would need to turn off their car to allow the key chain tag to be scanned and thus connect the purchase to their rewards account. As such, adding a rewards accounts to a retail pharmacy purchase adds additional manual steps to the overall transaction, which slows the total time necessary to complete the transaction It is with respect to these and other considerations that the present improvements are desired.

SUMMARY

In view of the forgoing, a system and method are disclosed for recognizing a pharmacy customer and the prescriptions the pharmacy customer is authorized to pick up and for facilitating purchase of the prescriptions.

An exemplary embodiment of a retail pharmacy sales device is provided. The retail pharmacy sales device may include a customer identification module to receive a customer identification corresponding to a customer and query a customer database for customer information and a pharmacy order associated with the customer, a prescription sales module to send a pharmacy order including an indication of a prescription corresponding to the pharmacy order to a mobile device and receive a customer authorization from the mobile device, the customer authorization including an indication that a purchase of the prescription is authorized based on the pharmacy order, and an order processing module to process the purchase for the pharmacy order based on the customer authorization.

An exemplary embodiment of a mobile device is also provided. The mobile device may include a customer authorization module to communicate a customer identification to a retail pharmacy sales device, the customer identification corresponding to a customer, a pharmacy order acknowledgment module to receive a pharmacy order including an indication of a prescription to be purchased, and a prescription purchase module to communicate a customer authorization for the pharmacy order to the retail pharmacy sales device.

An exemplary embodiment of a machine-readable storage medium is also provided. The machine-readable storage medium may include instructions that when executed by a computing device, cause the computing device to communicate a customer identification to a retail pharmacy sales device, the customer identification corresponding to a customer, receive a pharmacy order including an indication of a prescription to be purchased, and communicate a customer authorization for the pharmacy order to the retail pharmacy sales device.

An exemplary method implemented by a retail pharmacy sales device is also provided. The method may include receiving a customer identification corresponding to a customer from a mobile device, querying a customer database for customer information and a pharmacy order associated with the customer, sending the pharmacy order to the mobile device, the pharmacy order including an indication of a prescription corresponding to the pharmacy order, receiving a customer authorization from the mobile device, the customer authorization including an indication that a purchase of the prescription is authorized based on the pharmacy order, and processing the purchase for the pharmacy order based on the customer authorization.

BRIEF DESCRIPTION OF THE DRAWINGS

By way of example, specific embodiments of the disclosed device will now be described, with reference to the accompanying drawings, in which:

FIGS. 4-5 are flow diagrams illustrating exemplary methods for configuring an alarm panel in accordance with the present disclosure.

DETAILED DESCRIPTION

Figure 1:
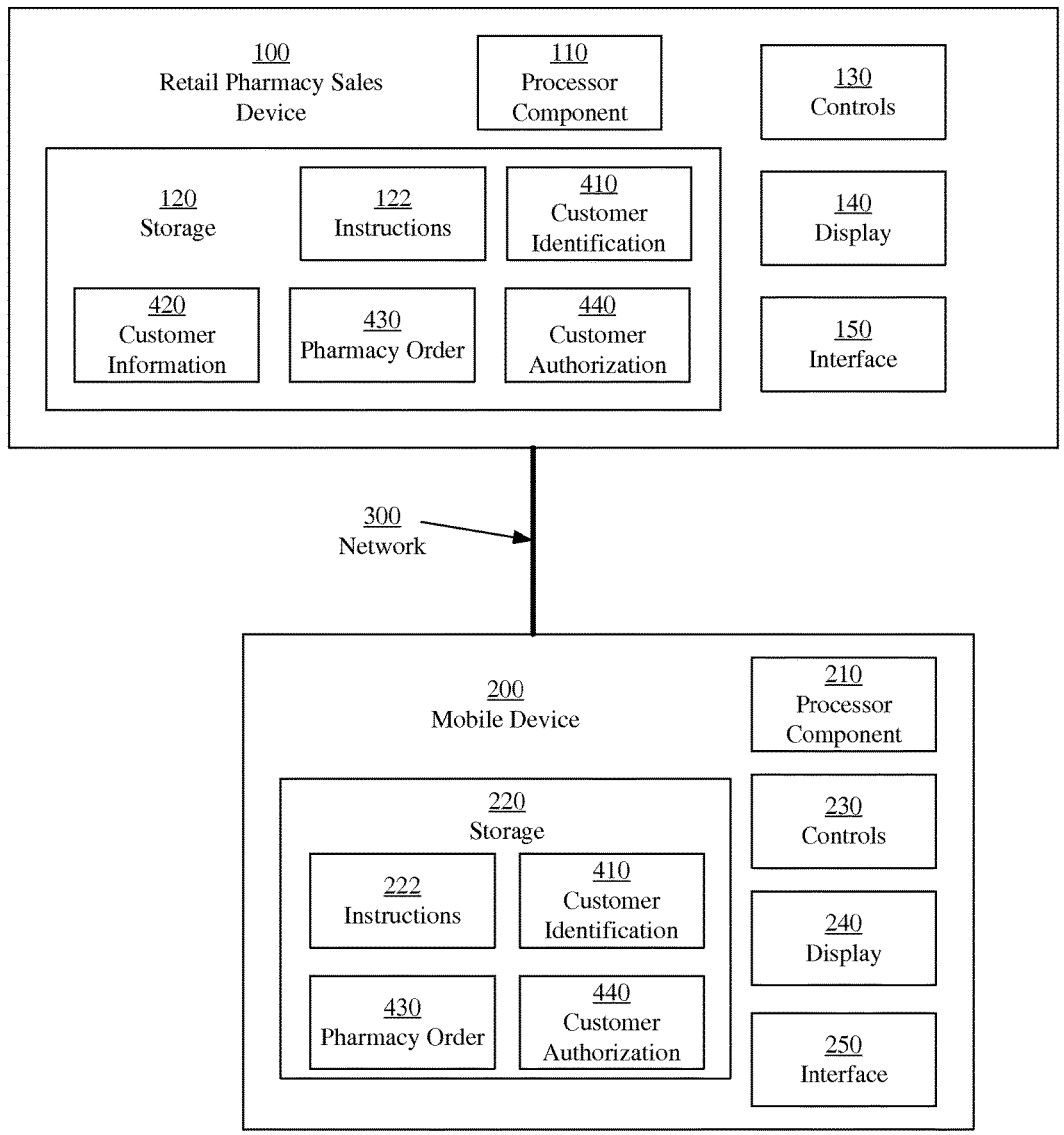
FIG. 1 is a block diagram illustrating an alarm panel configuration system in accordance with the present disclosure.

Systems and methods for the recognition and sales of prescriptions to pharmacy customers in accordance with the present disclosure will now be described more fully hereinafter with reference to the accompanying drawings. In general, the disclosed systems and methods provide that a pharmacy customer and the customer's authorization for picking up prescriptions may be identified. More specifically, a first customer and one or more additional customers for whose prescriptions the first customer is authorized to pick up may be identified. Additionally, the systems and methods may facilitate mobile payment of the transaction and associating a rewards account to the transaction.

It is important to note, however, that the disclosed systems and methods may be embodied in many different forms and should not be construed as limited to the embodiments set forth herein. Rather, these embodiments are provided so that this disclosure will be thorough and complete, and will fully convey the scope of the claims. In the drawings, like numbers refer to like elements throughout.

A first exemplary configuration in accordance with the present disclosure is depicted in FIG. 1. The disclosed retail pharmacy sales system 1000 may include a retail pharmacy sales device 100 and a mobile device 200 operably coupled via network connection 300. Each of the retail pharmacy sales device 100 and the mobile device 200 may be any of a variety of types of computing devices. For example, without limitation, the retail pharmacy sales device 100 and/or the mobile device may be a server, a desktop computer, a data entry terminal, a laptop computer, a netbook computer, a tablet computer, a smart phone, a self-check out kiosk, or the like. It is important to note, that with some examples, the retail pharmacy sales device 100 may be a computing device provided by the retail pharmacy and used by the retail pharmacy staff (e.g., pharmacist, sales clerk, or the like) while a customer may provide the mobile device 200 and use the mobile device 200 to facilitate the transaction. As another example, the pharmacy may provide the mobile device 200, which may be made available to customers to facilitate the transaction. More specifically, the mobile device 200 may be a smart phone, a tablet computer, an in store kiosk, or the like, that may be provided by the pharmacy as a convenience to customers and subsequently used to facilitate retail pharmacy transactions as described herein.

As depicted, the retail pharmacy sales device 100 and the mobile device 200 exchange signals conveying customer data, customer authorization information, and/or prescription order information through network 300. However, one of more of the retail pharmacy sales device 100 and/or the mobile device 200 may exchange signals unrelated to a retail prescription sale with each other and/or with still other computing devices (not shown) through the network 300 or through another network connection (not shown).

In various examples, the network 300 may be a may be a single network possibly limited to extending within a defined area (e.g., retail pharmacy location, or the like) or other relatively limited area, a combination of connected networks possibly extending a considerable distance, and/or may include the Internet. Thus, the network 300 may be based on any of a variety (or combination) of communications technologies by which signals may be exchanged, including without limitation, wired technologies employing electrically and/or optically conductive cabling, and wireless technologies employing radio frequency, near filed communication, Bluetooth, infrared, or other forms of wireless transmission.

In various embodiments, the retail pharmacy sales device 100 incorporates one or more of a processor component 110, storage 120, controls 130, a display 140, and an interface 150 to couple the retail sales device 100 to the network 300. The storage 120 stores one or more instructions 122, customer identification 410, customer information 420, pharmacy order 430, and customer authorization 440. In various embodiments, the mobile device 200 incorporates one or more of a processor component 210, storage 220, controls 230, a display 240, and an interface 250 to couple the mobile device 200 to the network 300. The storage 220 stores one or more instructions 222, the customer identification 410, the pharmacy order 430, and the customer authorization 440.

In the retail pharmacy sales device 100, the instructions 122 may correspond to a sequence of instructions operative on the processor component 110 to implement logic to perform various functions. In executing the instructions 122, the processor component 110 receives the customer identification 410 corresponding to a customer and queries a customer database (refer to FIG. 2) for the customer information 420 and the pharmacy order 430 associated with the customer.

Furthermore, in executing the instructions 122, the processor component 110 sends the pharmacy order 430, including an indication of a prescription corresponding to the pharmacy order 430 to the mobile device 200 and receives the customer authorization 440 from the mobile device 220. The customer authorization 440 may include the customer authorization including an indication that a purchase of the prescription is authorized based on the pharmacy order 430. Additionally, in executing the instructions 122, the processor component 110 processes the purchase for the pharmacy order 430 based on the customer authorization 440.

In the mobile device 200, the instructions 222 may correspond to a sequence of instructions operative on the processor component 210 to implement logic to perform various functions. In executing the instructions 222, the processor component 210 communicates the customer identification 410 to the retail pharmacy sales device 100, where the customer identification 410 corresponds to a customer of the pharmacy and/or identifies the customer to the pharmacy.

Furthermore, in executing the instructions 222, the processor component 210 receives the pharmacy order 430 including an indication of the prescription to be purchased. Additionally, in executing the instructions 222, the processor component 210 communicates the customer authorization 440 to the retail pharmacy sales device 100.

In various embodiments, each of the processor components 110 and 210 may include any of a wide variety of commercially available processors. Further, one or more of these processor components may include multiple processors, a multi-threaded processor, a multi-core processor (whether the multiple cores coexist on the same or separate dies), and/or a multi-processor architecture of some other variety by which multiple physically separate processors are in some way linked.

In various embodiments, each of the storages 120 and 220 may be based on any of a wide variety of information storage technologies, possibly including volatile technologies requiring the uninterrupted provision of electric power, and possibly including technologies entailing the use of machine-readable storage media that may or may not be removable. Thus, each of these storages may include any of a wide variety of types (or combination of types) of storage device, including without limitation, read-only memory (ROM), random-access memory (RAM), dynamic RAM (DRAM), Double-Data-Rate DRAM (DDR-DRAM), synchronous DRAM (SDRAM), static RAM (SRAM), programmable ROM (PROM), erasable programmable ROM (EPROM), electrically erasable programmable ROM (EEPROM), flash memory, polymer memory (e.g., ferroelectric polymer memory), ovonic memory, phase change or ferroelectric memory, silicon-oxide-nitride-oxide-silicon (SONOS) memory, magnetic or optical cards, one or more individual ferromagnetic disk drives, or a plurality of storage devices organized into one or more arrays (e.g., multiple ferromagnetic disk drives organized into a Redundant Array of Independent Disks array, or RAID array). It should be noted that although each of these storages is depicted as a single block, one or more of these may include multiple storage devices that may be based on differing storage technologies. Thus, for example, one or more of each of these depicted storages may represent a combination of an optical drive or flash memory card reader by which programs and/or data may be stored and conveyed on some form of machine-readable storage media, a ferromagnetic disk drive to store programs and/or data locally for a relatively extended period, and one or more volatile solid state memory devices enabling relatively quick access to programs and/or data (e.g., SRAM or DRAM). It should also be noted that each of these storages may be made up of multiple storage components based on identical storage technology, but which may be maintained separately as a result of specialization in use (e.g., some DRAM devices employed as a main storage while other DRAM devices employed as a distinct frame buffer of a graphics controller).

Furthermore, the storages 120 and 220 may be located within the respective computing devices, or may be external to the respective computing devices. In some examples the storages may be on the network, accessible over the Internet, over a secured network (e.g., VPN, intranet, or the like).

In various embodiments, each of the interfaces 150 and 250 may employ any of a wide variety of signaling technologies enabling computing devices to be coupled to other devices as has been described. Each of these interfaces may include circuitry providing at least some of the requisite functionality to enable such coupling. However, each of these interfaces may also be at least partially implemented with sequences of instructions executed by corresponding ones of the processor components (e.g., to implement a protocol stack or other features). Where electrically and/or optically conductive cabling is employed, these interfaces may employ signaling and/or protocols conforming to any of a variety of industry standards, including without limitation, RS-232C, RS-422, USB, Ethernet (IEEE-802.3) or IEEE-1394. Where the use of wireless signal transmission is entailed, these interfaces may employ signaling and/or protocols conforming to any of a variety of industry standards, including without limitation, IEEE 802.11a, 802.11b, 802.11g, 802.16, 802.20 (commonly referred to as "Mobile Broadband Wireless Access"); Bluetooth; ZigBee; or a cellular radiotelephone service such as GSM with General Packet Radio Service (GSM/GPRS), CDMA/1xRTT, Enhanced Data Rates for Global Evolution (EDGE), Evolution Data Only/Optimized (EV-DO), Evolution For Data and Voice (EV-DV), High Speed Downlink Packet Access (HSDPA), High Speed Uplink Packet Access (HSUPA), 4G LTE, etc.

In some examples, the network 300 may be a secure network connection between the retail pharmacy sales device 100 and the mobile device 200. More specifically, the network 300 may be established between the retail pharmacy sales device 100 and the mobile device 200 using various network technologies and/or protocols designed to prevent the data transmitted between the devices from being made know to unintended computing devices. For example, with some embodiments, the interfaces 150 and 250 may establish the network 300 (e.g., in an ad-hoc fashion, or the like) using various wireless connection technologies (WIFI, Bluetooth, or the like). This network may be encrypted and/or otherwise secured to form a secured network connection. As another example, the network 300 may be established through an intermediate server (not shown) configured to authenticate and secure the connection. As such, the interfaces 150 and/or 250 may be referred to as secure link modules that are configured to establish a secure network connection between the retail pharmacy sales device 100 and the mobile device 200.

Figure 2:
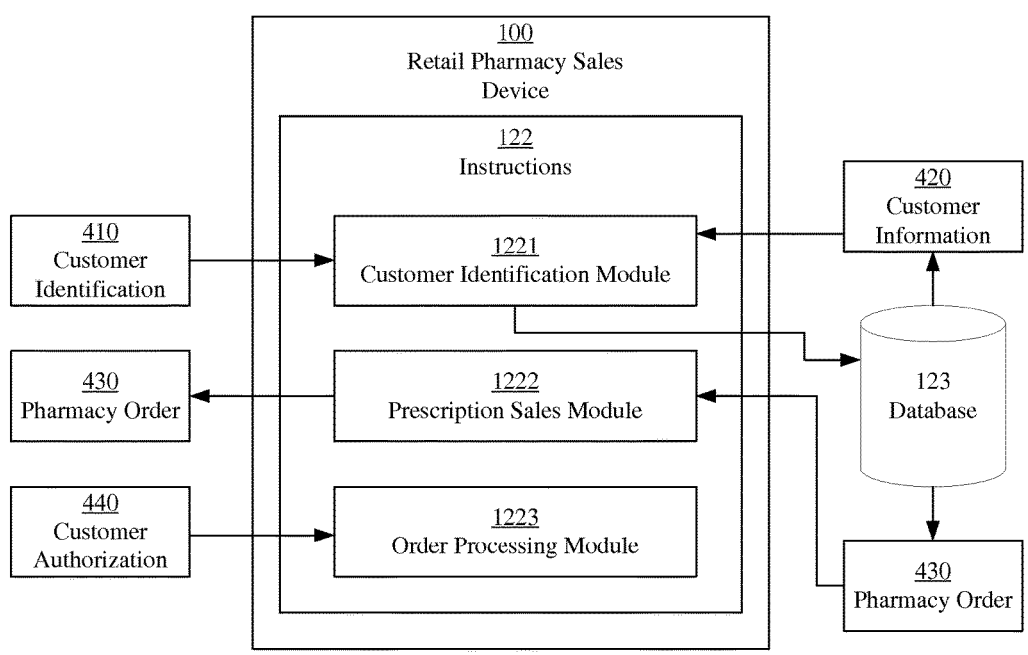
FIGS. 2-3 are block diagrams illustrating portions of the system shown in FIG. 1 is greater detail, all arranged in accordance with the present disclosure.
Figure 3:
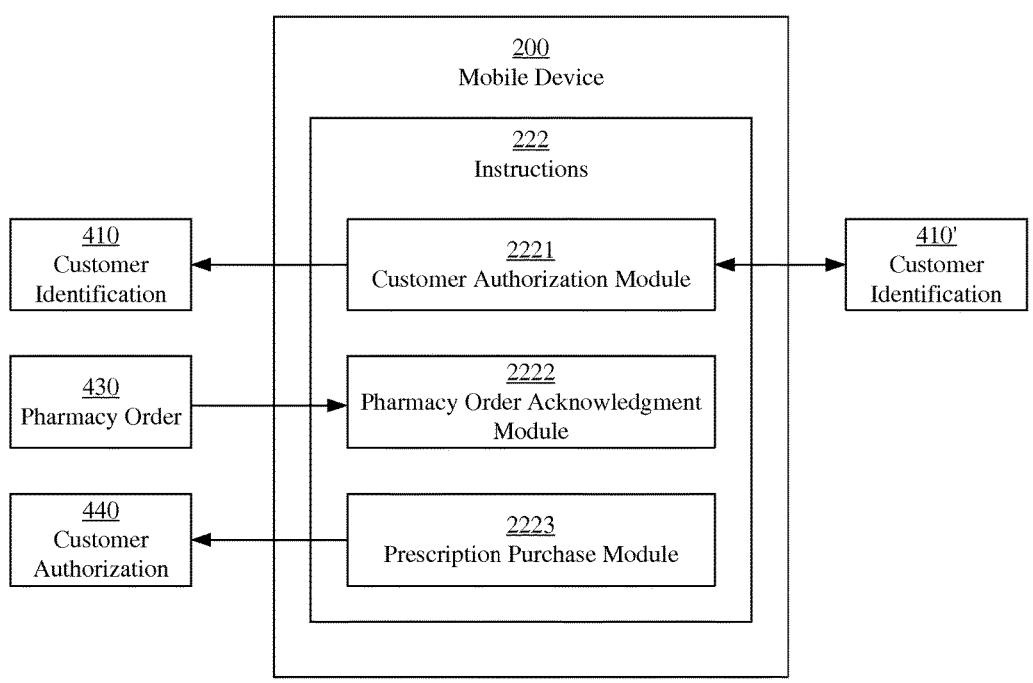

FIGS. 2-3 are each a simplified block diagram of a portion of an embodiment of the system 1000 of FIG. 1. Each of these figures depicts aspects of the operation of identifying a retail pharmacy sales customer, the prescriptions for which the customer is authorized to pick up, and completing a purchase of the prescriptions. More specifically, FIG. 2 depicts aspects of the operation of the retail pharmacy sales device 100 while FIG. 3 depicts aspects of the operation of the mobile device 200.

Turning more specifically to FIG. 2, the instructions 122 may include a customer identification module 1221, a prescription sales module 1222, and an order processing module 1223. Additionally, the retail pharmacy sales device 100 may include (e.g., in storage 120) or be otherwise communicatively connected to database 123. It is important to note, that the database 123 may be located internal to the device 100 or external. For example, with some embodiments, the database 123 may reside on a central server (not shown) and accessed via network 300. In particular, with some examples, the retail pharmacy sales device 100 may receive information from the mobile device 200 and provide this information to another computing device (e.g., a cloud based computing device, or the like.) This cloud based computing device may then perform some of the operations described herein in conjunction with the retail pharmacy sales device 100.

The customer identification module 1221 may receive the customer identification 410 from the mobile device 200. In general, the customer identification may be any indicator that positively identifies the customer to the pharmacy. For example, the customer identification 410 may be a scannable indicator (e.g., displayed on the mobile device 200) that may be scanned by the retail pharmacy sales device 100 to identify the customer. As another example, the customer identification 410 may be credentials associated with the customers account (e.g., local, online, or the like) at the pharmacy. Additionally, the pharmacy customer identified may be a first pharmacy customer and the customer identification 410 may include an indication of other pharmacy customers for who the first pharmacy customer is authorized to pick up prescriptions. This is explained in greater detail below.

The customer identification module 1221 may query the database 123 for the customer information 420 and the pharmacy order 430 associated with the identified customer. In general, the customer information may include information helpful to facilitating the pharmacy transaction. For example the customer information may include a pharmacy rewards account, preferred payment information, preference regarding counseling from a pharmacist, or the like. It is important to note, that the customer information may correspond to both the first customer and the additional customers for which the first customer is authorized to pick up prescriptions. For example, it is envisioned, that a customer may pick up a prescription for himself, and a friend. Under this scenario, both parties may have separate pharmacy rewards accounts. As such, the customer identification module 1221 may query the database 123 for the rewards accounts corresponding to each customer.

In addition to rewards account information, the customer information 420 may include coupons available for the customer to use, complementary purchase offers, or the like.

The prescription sales module 1222 may receive the pharmacy order 430. As noted, the pharmacy order may include a prescription for the identified customer, or other customers for which the identified customer is authorized to pick up prescriptions. In some examples, the pharmacy order may include indication of the prescriptions ready to picked up. Additionally, the pharmacy order may include an indication of prescriptions waiting to be filled.

The prescription sales module 1222 may communicate the pharmacy order 430 to the mobile device 200. With some examples, the prescription sales module 1222 may communicate a summary of the pharmacy order 430 to the mobile device 200. The summary may list the prescriptions being picked up and request any acknowledgments necessary for regulatory purposes.

Additionally, with some examples, the prescription sales module 1222 may send the pharmacy order 430 to the mobile device before the customer identification is received. For example, the prescription sales module 1222 may send a message (e.g., SMS message, MMS message, or the like) to the mobile device 200 indicating that a prescription is available to be picked up. The message may include a link to open an application on the mobile device 200 to facilitate the transactions (e.g., refer to FIG. 3).

The order processing module 1223 may receive the customer authorization 440 from the mobile device 200. The customer authorization 440 may include an indication that the customer authorizes a purchase of the prescription. Additionally, the customer authorization may include an indication of the method for purchasing (e.g., credit card payment, bank account information, PayPal®, gift card, or the like) as well as an electronic signature for the purchase. Additionally, the order processing module 1223 may process the purchase of the prescriptions and add the purchases to the corresponding rewards accounts.

Turning more specifically to FIG. 3 the instructions 222 may include a customer authorization module 2221, a pharmacy order acknowledgment module 2222, and a prescription purchase module 2223. The customer authorization module 2221 may communicate the customer identification 410 to the retail pharmacy sales device 100. As described above, the customer identification may include indications (e.g., scannable indicator, account credentials, or the like) to identify the customer to the pharmacy. For example, with some embodiments, the customer authorization module 2221 may be configured to generate a scannable indicator (QR code, UPC code, or the like) that may be scanned by the retail pharmacy sales device 100 to receive the customer identification 410.

Additionally, the customer authorization module 2221 may be configured to receive customer identification 410' corresponding to another customer for which the mobile device 200 is authorized to pickup prescriptions for. In some examples, the customer authorization module 2221 may include an interface configured to allow demographic information related to the other customer (e.g., corresponding to the customer identification 410') to be input into the customer authorization module 2221. For example, the customer authorization module 2221 may be configured to receive demographic information (e.g., name, address, birthdate, or the like) corresponding to another customer. The customer authorization module 2221 may contact a central server (not shown) to alert the server than the customer identification 410' has been added to the mobile device 200.

For example, the central server may be contacted over the Internet, or the like. The central server may alert (e.g., via text message, email, interactive voice response, or the like) the customer corresponding to the customer identification 410' that the mobile device 200 has been authorized to pickup prescriptions on their behalf.

As an example, a customer of the pharmacy may desire to authorize their family member or friend to pick up prescriptions for them. As such, the customer may give their demographic information to their friend, for input into the authorization module 2221. The authorization module 2221 may receive the demographic information and generate the customer identification 410' corresponding to the family member or friend. Generation of the customer identification 410' may include communicating with a central server (not shown) to retrieve information related to the customer. Additionally, the customer authorization 410' may include an indication of the preferred payment method for the authorized prescriptions. For example, the customer authorization 410' may include an indication that the prescriptions may be purchases with the payment method associated with the customers account (e.g., credit card information saved online, or the like). Accordingly, a first customer may pick up prescription(s) from the pharmacy for a friend and/or family member and have the prescriptions charged to the family member or friends credit card.

The pharmacy order acknowledgment module 2222 may receive the pharmacy order 430, including an indication of the prescription(s) to be purchased from the retail pharmacy sales device 100. With some examples, the pharmacy order acknowledgement module 2222 may request authorization and/or acknowledgment from the customer consenting to various regulatory requirements or disclosures corresponding to the prescription(s). For example, the pharmacy order acknowledgment module 2222 may cause a popup to be displayed requesting consent, or the like.

In some examples, the pharmacy order 430 may include a listing of all available prescriptions for which the customer is authorized to pick up. The pharmacy order acknowledgement module 2222 may be configured to present options for viewing and/or selecting to pick up one or more of the listed available prescriptions.

The prescription purchase module 2223 may communicate the customer authorization 440 to the retail pharmacy sales device. The customer authorization 440 may include an indication that the customer authorizes a purchase of the prescription. Additionally, the customer authorization 440 may include an indication of the method for purchasing (e.g., credit card payment, bank account information, PayPal®, gift card, or the like) as well as an electronic signature for the purchase. With some examples, the prescription purchasing module 2223 may be configured to capture an electronic signature (e.g., record a pin number, capture an image of a signature made on a touch screen, or the like) and communicate the electronic signature to the retail pharmacy sales device 100.

With some examples, the prescription purchasing module 2223 may be configured to store a credit card for use in making purchases. Accordingly, the credit card information may be communicated to the retail pharmacy sales device to complete purchases and the customer would not need to reenter the credit card information each time a prescription is picked up.

FIGS. 4-5 are each a simplified block diagram of example logic flows that may be performed by various portions of the system 1000 of FIG. 1. Each of these logic flows depicts aspects of a method for identifying a retail pharmacy sales customer, the prescriptions for which the customer is authorized to pick up, and completing a purchase of the prescriptions. More specifically, FIG. 4 depicts a method implemented by the retail pharmacy sales device 100 while FIG. 5 depicts a method implemented by the mobile device 200.

Referring now to FIG. 4, a flow diagram illustrating an exemplary method 500 in accordance with the present disclosure is shown. At a first block 510, receive a customer identification corresponding to a customer from a mobile device; the retail pharmacy sales device 100 may receive the customer identification 410. For example, at block 510, the customer identification module 1221 may receive the customer identification 410.

Continuing from block 510 to block 520, query a customer database for customer information and a pharmacy order associated with the customer; the retail pharmacy sales device 100 queries the database 123 for a pharmacy order associated with the customer. For example, the customer identification module 1221 may query the database 123 for the pharmacy order 430.

In some examples, the customer identification module 1221 may be configured to identify customers who have "checked into" the store. For example, customers can check in using a mobile app (e.g., smart phone app, tablet app, or the like). A central server (not shown) may receive an indication that the customer checked in (e.g., via the Internet, or the like) and alert the customer identification module 1221 that a particular customer checked in. As another example, the customer identification module 1221 may be configured to detect and/or determine a customer has entered the store or is present in the store based on GPS coordinates, RFID signals, or the like. The customer identification module 1221 may then query the database 123 for a pharmacy order associated with the customer. In some examples, the customer identification module 1221 may be configured to only identify customers who check in and also have an existing pharmacy order.

As an optional step between blocks 510 and 520, the customer identification module 1221 may be configured to receive demographic information, a security setting (e.g., phrase, image, code, or the like) corresponding to the identified customer who checked in. Such demographic information and/or security setting can be used to authenticate the customer.

Continuing from block 520 to block 530, send the pharmacy order to the mobile device; the retail pharmacy sales device 100 sends the pharmacy order 430 to the mobile device 200. For example, the prescription sales module 1222 may send the pharmacy order 430 to the mobile device 200.

Continuing from block 530 to block 540, receive a customer authorization from the mobile device; the retail pharmacy sales device 100 receives the customer authorization 440. For example, the order processing module 1223 may receive the customer authorization 440.

Referring now to FIG. 5, a flow diagram illustrating an exemplary method 600 in accordance with the present disclosure is shown. At a first block 610 in the flow diagram, communicate a customer identification to a retail pharmacy sales device; the mobile device 200 may communicate the customer identification 410 to the retail pharmacy sales device 100. For example, the customer authorization module 2221 may communicate the customer identification 410 to the retail pharmacy sales device 100.

Continuing from block 610 to block 620, receive a pharmacy order including an indication of a prescription to be purchased from the retail sales device; the mobile device may receive the pharmacy order 430. For example, the pharmacy order acknowledgement module 2222 may receive the pharmacy order 430 from the retail pharmacy sales device 100.

Continuing from block 620 to block 630, communicate a customer authorization for the pharmacy order to the retail pharmacy sales device, the mobile device may communicate the customer authorization 440 to the retail pharmacy sales device 100. For example, the prescription purchase module 2223 may communicate the customer authorization 440 to the retail pharmacy sales device 100.

Thus, a retail pharmacy sales system in which a customer can use a mobile device (e.g., smart phone, or the like) to identify himself or herself and also to identify others to which they are authorized to pick up prescriptions for is disclosed.

As used herein, an element or step recited in the singular and proceeded with the word "a" or "an" should be understood as not excluding plural elements or steps, unless such exclusion is explicitly recited. Furthermore, references to "one embodiment" of the present invention are not intended to be interpreted as excluding the existence of additional embodiments that also incorporate the recited features.

The various embodiments or components described above, for example, the retail pharmacy sales device 100 and the mobile device 200 may be implemented as part of one or more computer systems. Such a computer system may include a computer, an input device, a display unit and an interface, for example, for accessing the Internet. The computer may include a microprocessor. The microprocessor may be connected to a communication bus. The computer may also include memories. The memories may include Random Access Memory (RAM) and Read Only Memory (ROM). The computer system further may include a storage device, which may be a hard disk drive or a removable storage drive such as a floppy disk drive, optical disk drive, and the like. The storage device may also be other similar means for loading computer programs or other instructions into the computer system. As used herein, the term "module" or "software" software" includes any computer program stored in memory for execution by a computer, such memory including RAM memory, ROM memory, EPROM memory, EEPROM memory, and non-volatile RAM (NVRAM) memory. The above memory types are exemplary only, and are thus not limiting as to the types of memory usable for storage of a computer program.

While certain embodiments of the disclosure have been described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:

1. A retail pharmacy sales device, comprising:
   a processor component; and
   storage storing instructions that, when executed, cause the processor component to:
   detect that a first customer has checked into a retail pharmacy store by receiving a first customer identification of the first customer that identifies the first customer and that includes a scannable indicator displayed on a mobile device of the first customer;
   identify a second customer and verify that the first customer is authorized to pick up a prescription for the second customer based on the first customer providing a second customer identification from the mobile device of the first customer, the second customer identification including a payment account associated with the second customer;

query a customer database for a pharmacy order and a rewards account associated with the second customer based on the first and second customer identifications, wherein the pharmacy order includes the prescription for the second customer that is available for pick up in the retail pharmacy store by the first customer;

send the pharmacy order and a message to the mobile device of the first customer, the pharmacy order including an indication of the prescription for the second customer, the message indicating that the prescription for the second customer is available for pick up by the first customer and including a link to open an application on the mobile device of the first customer to facilitate transactions including a mobile payment with the payment account associated with the second customer;

receive a customer authorization from the mobile device of the first customer, the customer authorization including an indication that a purchase of the prescription for the second customer is authorized based on the pharmacy order, wherein the second customer is alerted that the second customer identification corresponding to the second customer has been added to the mobile device of the first customer and the mobile device of the first customer has been authorized to be used to pick up the prescription for the second customer; and process the purchase for the pharmacy order based on the customer authorization by processing the purchase of the prescription for the second customer using the mobile payment with the payment account associated with the second customer and adding the purchase to the rewards account associated with the second customer.

2. The retail pharmacy sales device of claim 1, wherein instructions that, when executed, cause the processor component to establish a secure network connection between the retail pharmacy sales device and the mobile device, wherein the first customer identification, the second customer identification, and the customer authorization are received through the secure network connection.

3. The retail pharmacy sales device of claim 2, wherein the pharmacy order is communicated to the mobile device through the secure network connection.

4. The retail pharmacy sales device of claim 1, wherein the scannable indicator is selected from the group of a QR code, a bar code, and a UPC code.

5. The retail pharmacy sales device of claim 1, wherein instructions that, when executed, cause the processor component to process the purchase of the prescription for the second customer using either (i) a credit card associated with the second customer or (ii) a mobile payment system associated with the second customer.

6. The retail pharmacy sales device of claim 1, wherein instructions that, when executed, cause the processor component to receive an indication of a payment method and an electronic signature for purchase of the prescription for the second customer from the mobile device of the first customer.

7. The retail pharmacy sales device of claim 6, wherein the payment method is selected from the group consisting of credit card information, debit card information, or checking account information.

8. The retail pharmacy sales device of claim 1, wherein the pharmacy order includes a listing of all available prescriptions for which the first customer is authorized to pick up at the retail pharmacy store.

9. A mobile device of a first customer, comprising:
a processor component and
storage storing instructions that, when executed, cause the processor component to:
communicate a first customer identification to a retail pharmacy sales device when the first customer enters a retail pharmacy store, wherein the retail pharmacy sales device detects that the first customer has checked into the retail pharmacy store by receiving the first customer identification of the first customer that identifies the first customer and that includes a scannable indicator displayed on a mobile device of the first customer, identifies a second customer and verifies that the first customer is authorized to pick up a prescription at the retail pharmacy store for the second customer based on the first customer providing a second customer identification from the mobile device of the first customer, the second customer identification including a payment account associated with the second customer;
receive a pharmacy order including an indication of the prescription for the second customer that is available for pick up at the retail pharmacy store by the first customer and to be purchased using the payment account associated with the second customer, wherein a purchase of the prescription is added to a rewards account associated with the second customer; and
communicate a customer authorization for the pharmacy order to the retail pharmacy sales device, the customer authorization including an indication of the payment account associated with the second customer and authorization for the first customer to pick up the prescription for the second customer, wherein the second customer is alerted that the second customer identification corresponding to the second customer has been added to the mobile device of the first customer and the mobile device of the first customer has been authorized to be used to pick up the prescription for the second customer.

10. The mobile device of claim 9, wherein instructions that, when executed, cause the processor component to establish a secure network connection between the mobile device of the first customer and the retail pharmacy sales device, wherein the first customer identification and the customer authorization are communicated to the retail pharmacy sales device through the secure network connection.

11. The mobile device of claim 9, wherein instructions that, when executed, cause the processor component to generate the scannable indicator corresponding to the first customer identification.

12. The mobile device of claim 11, wherein the scannable indicator is selected from the group consisting of a QR code, a bar code, and a UPC code.

13. The mobile device of claim 9, wherein instructions that, when executed, cause the processor component to receive the indication that the prescription for the second customer is desired for pick up by the first customer and to communicate the indication that the prescription for the second customer is desired for pick up by the first customer to the retail pharmacy sales device.

14. The mobile device of claim 9, wherein instructions that, when executed, cause the processor component to receive the indication of the payment method associated with the second customer for completing the pharmacy order and to communicate the indication of the payment account associated with the second customer to the retail pharmacy sales device.

15. The mobile device of claim 14, wherein instructions that, when executed, cause the processor component to receive an electronic signature authorizing the pharmacy order using the payment account associated with the second customer and communicate the electronic signature to the retail pharmacy sales device.

16. The mobile device of claim 15, further comprising a touch screen, wherein the electronic signature is received at least in part based on input received from the touch screen.

17. The mobile device of claim 9, wherein the pharmacy order includes a listing of all available prescriptions which the first customer is authorized to pick up at the retail pharmacy store.

18. A method implemented by a retail pharmacy sales device, the method comprising:
   automatically detecting that a first customer has checked into a retail pharmacy store by receiving a first customer identification of the first customer that identifies the first customer and that includes a scannable indicator displayed on a mobile device of the first customer;
   identifying a second customer and verifying that the first customer is authorized to pick up a prescription at the retail pharmacy store for the second customer based on the first customer providing a second customer identification from the mobile device of the first customer, the second customer identification including a payment account associated with the second customer;
   querying a customer database for a pharmacy order and a rewards account associated with the second customer based on the first and second customer identifications;
   sending the pharmacy order and a message to the mobile device of the first customer, the pharmacy order including an indication of the prescription corresponding to the pharmacy order, wherein the prescription is for the second customer, and the message indicates that the prescription for the second customer is available for pick up in the retail pharmacy store by the first customer and includes a link to open an application on the mobile device of the first customer to facilitate transactions including a mobile payment with the payment account associated with the second customer;
   receiving a customer authorization from the mobile device of the first customer, the customer authorization including an indication that a purchase of the prescription for the second customer is authorized by the second customer based on the pharmacy order, wherein the second customer is alerted that the second customer identification corresponding to the second customer has been added to the mobile device of the first customer and the mobile device of the first customer has been authorized to be used to pick up the prescription for the second customer; and
   processing the purchase for the pharmacy order based on the customer authorization, wherein the prescription for the second customer is purchased using the mobile payment with the payment account associated with the second customer and the purchase is added to the rewards account associated with the second customer.

19. The method of claim 18, further comprising:
   receiving a request for a secure network connection from the mobile device; and
   establishing the secure network connection between the retail pharmacy sales device and the mobile device, wherein the first customer identification, the second customer identification, and the customer authorization are received through the secure network connection.

20. A method comprising:
   detecting that a first customer has checked into a retail pharmacy store by receiving a first customer identification of the first customer that identifies the first customer and that includes a scannable indicator displayed on a mobile device of the first customer;
   determining if a first prescription associated with the first customer is available for pick up by the first customer;
   identifying a second customer and verifying that the first customer is authorized to pick up prescriptions for the second customer based on the first customer providing a second customer identification from the mobile device of the first customer, the second customer identification including a payment account associated with the second customer;
   determining if a second prescription associated with the second customer is available for pick up by the first customer;
   sending a message to the mobile device of the first customer to alert the first customer that the second prescription associated with the second customer is available for pick up by the first customer and to include a link to open an application on the mobile device of the first customer to facilitate transactions including a mobile payment with the payment account associated with the second customer;
   alerting the second customer that the second customer identification corresponding to the second customer has been added to the mobile device of the first customer and the mobile device of the first customer has been authorized to be used to pick up the second prescription on behalf of the second customer;
   processing a purchase of the second prescription associated with the second customer using the payment account associated with the second customer;
   adding the purchase of the second prescription to a rewards account associated with the second customer; and
   providing the second prescription associated with the second customer to the first customer.

21. The method of claim 20, wherein detecting comprises determining a location of the first customer using GPS.

22. The method of claim 20, wherein detecting comprises determining a location of the first customer using RFID.

23. The method of claim 20, wherein identifying comprises receiving demographic information of the second customer.

24. The method of claim 20, wherein alerting the second customer comprises providing a text message to a mobile device of the second customer.

25. The method of claim 20, wherein alerting the second customer comprises providing an email message to the second customer.

26. The method of claim 20, wherein alerting the second customer comprises providing an interactive voice message to the second customer.

27. The method of claim 20, wherein the scannable indicator is selected from the group of a QR code, a bar code, and a UPC code.

\* \* \* \* \*